(12) United States Patent
Farley et al.

(10) Patent No.: US 9,877,648 B2
(45) Date of Patent: Jan. 30, 2018

(54) CONTACT LENS MOUNTING SPECULUM FOR VITREORETINAL SURGERY

(71) Applicant: NOVARTIS AG, Basel (CH)

(72) Inventors: Mark Farley, Lake Forest, CA (US); Steve Charles, Memphis, TN (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/858,878

(22) Filed: Sep. 18, 2015

(65) Prior Publication Data

US 2017/0079528 A1 Mar. 23, 2017

(51) Int. Cl.
| | | |
|---|---|---|
| A61B 3/00 | (2006.01) | |
| A61B 3/125 | (2006.01) | |
| A61B 3/13 | (2006.01) | |
| A61F 9/00 | (2006.01) | |
| A61B 17/02 | (2006.01) | |
| A61F 9/007 | (2006.01) | |

(52) U.S. Cl.
CPC ............ *A61B 3/125* (2013.01); *A61B 3/13* (2013.01); *A61B 17/0231* (2013.01); *A61F 9/0061* (2013.01); *A61F 9/00736* (2013.01)

(58) Field of Classification Search
USPC ................................................ 351/200–246
See application file for complete search history.

(56) References Cited

U.S. PATENT DOCUMENTS

| | | | |
|---|---|---|---|
| 4,856,872 A | 8/1989 | Spitznas et al. | 350/255 |
| 5,070,860 A | 12/1991 | Grounauer | |
| 5,085,013 A * | 2/1992 | Ascosi | B24B 13/0025 451/384 |
| 5,307,740 A * | 5/1994 | Yamamoto | G02C 7/021 101/126 |
| 5,336,215 A * | 8/1994 | Hsueh | A61F 9/009 606/10 |
| 7,338,170 B2 * | 3/2008 | Cech | A61B 3/12 351/218 |

(Continued)

FOREIGN PATENT DOCUMENTS

| | | |
|---|---|---|
| EP | 1295579 | 3/2003 |
| WO | 2012/031277 | 3/2012 |
| WO | 2012/170966 | 12/2012 |

OTHER PUBLICATIONS

Ocular Tolentino 30° Prism Vitrectomy Lens and Ocular Woldoff Prismatic Biconcave Vitrectomy Lens product page, downloaded from http://www.ocularinc.com/media/productmedia/390/5515%20-%20OLVS-3,3N%20Rev%20M.pdf; 2 pages, dated 2001.

(Continued)

*Primary Examiner* — Mohammed Hasan
(74) *Attorney, Agent, or Firm* — Baker Botts L.L.P.

(57) ABSTRACT

A contact lens is placed on a patient's eye during ophthalmic surgery, such as vitreoretinal surgery. The contact lens rests on a cornea of an eye of a patient during the surgery and is supported by a contact lens mounting speculum having multiple degrees of freedom to accommodate small movements of the eye while enabling alignment to an optical axis of the surgical microscope. The contact lens mounting speculum may be used with different patients, speculum blades, contact lenses (direct and indirect), and lens mounting positions.

12 Claims, 4 Drawing Sheets

(56) References Cited

U.S. PATENT DOCUMENTS

| | | | |
|---|---|---|---|
| 2005/0143718 A1* | 6/2005 | Rathjen | A61F 9/00825 606/5 |
| 2006/0192921 A1* | 8/2006 | Loesel | A61F 9/008 351/219 |
| 2013/0060254 A1 | 3/2013 | Juhasz | |
| 2014/0128853 A1* | 5/2014 | Angeley | A61F 9/00827 606/4 |

OTHER PUBLICATIONS

Volk Optical Inc., 45° Prism SSV® ACS®, Volk Optical Inc. catalog, downloaded from http://www.slideshare.net/kevainen/volk-catalog-april-09-lr, located on pp. 34, 36, and 45-46; 46 pages total, dated Apr. 2009.

Holoeye LC 2012 Spatial Light Modulator product page, downloaded from http://holoeye.com/spatial-light-modulators/lc-2012-spatial-light-modulator/; 3 pages, dated Sep. 2013.

Meadowlark Optics Transmissive Spatial Light Modulator product page, downloaded from http://www.meadowlark.com/transmissive-spatial-light-modulator-p-103?mid=16; 5 pages, dated Apr. 2015.

Varioptic—Electrowetting description, downloaded from http://www.varioptic.com/technology/electrowetting/; 3 pages, dated Jan. 2012.

Ohji et al., "Combining a Contact Lens and Wide-Angle Viewing System for a Wider Fundus View," Retina, The Journal of Retinal and Vitreous Diseases, vol. 31, No. 9; 3 pages, dated 2011.

Hisato Ohno, "Combined use of high-reflective index vitrectomy meniscus contact lens and a noncontact wide-angle viewing system in vitreous surgery," Clinical Ophthalmology 2011:5; 3 pages, dated 2011.

Austin Roorda, "Adaptive optics for studying visual function: A comprehensive review," Journal of Vision 11(5):6; 21 pages, 21 pages, dated 2011.

Volk Surgical MERLIN Surgical System brochure, 2013 Volk Optical Inc.; 4 pages, dated 2013.

Ocular Peyman-Wessels-Landers 132D Upright Vitrectomy Lens product page, 2003 Ocular Instruments; 1 page, dated 2003.

Ocular Landers 50° Prism Vitrectomy Lens product page, downloaded from http://www.ocularinc.com/ocular-landers-50-prism-vitrectomy-lens.html; 1 page, dated Jul. 2011.

* cited by examiner

CONTACT LENS MOUNTING SPECULUM FOR VITREORETINAL SURGERY

BACKGROUND

Field of the Disclosure

The present disclosure relates to ophthalmic surgery, and more specifically, to a contact lens mounting speculum for vitreoretinal surgery.

Description of the Related Art

In ophthalmology, eye surgery, or ophthalmic surgery, saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is performed on the eye and accessory visual structures. More specifically, vitreoretinal surgery encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic traction retinal detachment, vitreous hemorrhage, macular hole, detached retina, and complications of cataract surgery, among others.

During vitreoretinal surgery, an ophthalmologist typically uses a surgical microscope to view the fundus through the cornea, while surgical instruments that penetrate the sclera may be introduced to perform any of a variety of different procedures. The surgical microscope provides imaging and optionally illumination of the fundus during vitreoretinal surgery. The patient typically lies supine under the surgical microscope during vitreoretinal surgery and a speculum is used to keep the eye exposed by holding open the eyelids. Depending on a type of optical system used, the ophthalmologist has a given field of view of the fundus, which may vary from a narrow field of view to a wide field of view that can extend to peripheral regions of the fundus. For many types of vitreoretinal surgery using the surgical microscope, the surgeon may desire to have a very wide field of view of the fundus that extends beyond the equator and even out to the ora serrata. The optical system to provide the view of the fundus to the surgeon during vitreoretinal surgery may include a special ocular lens, of which three types are typically used: a direct (piano, flat, or magnifying) contact lens, an indirect non-contact lens, or an indirect contact lens.

A contact lens is in physical contact with the cornea and therefore has a concave surface to match the convex surface of the cornea. Typically a small amount of viscoelastic gel or saline fluid resides between the cornea and the contact lens to prevent unwanted extraneous interfacial reflections and to protect the cornea from dehydration.

A non-contact lens does not touch the eye and is spaced a certain working distance away from the eye.

A direct lens creates a non-inverted virtual image of the fundus behind the eye lens and generally in front of the fundus. The surgeon uses the surgical microscope to focus directly on this non-inverted virtual image, which is also referred to as an intermediate image plane or a focus plane. The direct lens enables the surgeon to directly view the fundus.

An indirect lens creates an inverted real image in the intermediate image plane in front of the eye lens (between the eye lens and the surgical microscope) and the surgeon uses the surgical microscope to focus on this intermediate image plane. The indirect lens enables the surgeon to indirectly view the fundus via the intermediate image plane. Since the indirect lens image is inverted to the viewer looking through the surgical microscope, typically an inverter lens is added to the surgical microscope to re-invert the fundus image to match the physical orientation of the eye during vitreoretinal surgery.

A direct contact lens can be placed onto the eye and is generally thin enough axially to normally remain in place on the cornea during vitreoretinal surgery. In certain optical systems, direct contact lenses have self-stabilizing features on the lens, such as base extensions that assist in keeping the direct contact lens from moving during surgery. However, a direct contact lens may not provide a very wide field of view into the fundus and of the retina and the field of view may be limited to about 30 degrees.

An indirect non-contact lens is not in contact with the eye and may be fixed to the surgical microscope. Therefore, the indirect non-contact lens may avoid issues of positional instability and additional resources involved (such as having a skilled surgical assistant to hold or reposition the lens) during vitreoretinal surgery. At least for these reasons, the indirect non-contact lens may be the ophthalmic surgical lens often chosen by many ophthalmologists. However, an indirect non-contact lens may be limited in the field of view of the fundus provided to the surgeon during vitreoretinal surgery. For example, the field of view using an indirect non-contact lens may be limited to less than about 140 degrees (full angle) and may be about 10 degrees less than wide angle contact lenses. Non-contact lenses do not eliminate corneal asphericity and may result in the surgeon rotating the eye farther than with a wide angle contact lens in order to view the peripheral retina.

In order to see beyond the region of fundus viewable at one time with the indirect non-contact lenses, the surgeon may employ various techniques during vitreoretinal surgery. For example, the surgeon may indent a peripheral region of sclera to push the fundus in the affected region into the field of view. The surgeon may rotate the eye off the optical axis to direct the field of view onto the desired peripheral region. In some instances, a combination of techniques is used. Frequently rotating the eye or depressing the sclera to view peripheral regions of the fundus are extraneous operations during vitreoretinal surgery that are performed for the purpose of obtaining a sufficient view. Scleral depression may result in additional trauma for the eye and may increase time of surgery, which may be undesirable for at least these reasons.

An indirect (wide-angle) contact lens may provide a much greater field of view of the fundus than other types of ophthalmic surgical lenses. Contact lenses may provide a field of view up to about 170 degrees (full angle), essentially out to the very edge of the retina at the ora serrata in a single image. However, contact lenses, which rest on the cornea during vitreoretinal surgery, are generally top-heavy due to their optical construction and typically move in angular and positional orientation after initial placement on the eye. Contact lenses may also be relatively sensitive to small movements by the patient during surgery, which is undesirable. Therefore, the surgeon oftentimes engages the help of an assistant, either to continually hold the contact lens in place or to frequently reposition the contact lens many times during the course of vitreoretinal surgery. Despite the large field of view afforded, the lack of positional stability and the additional involvement of a skilled surgical assistant to position the lens may be undesirable. At least for these reasons, the free-standing contact lens may be a less popular choice among vitreoretinal surgeons than a non-contact system.

SUMMARY

The disclosed embodiments of the present disclosure provide for illuminating and viewing the extreme periphery of the fundus during vitreoretinal surgery without implementing extraneous operations, without using additional skilled surgical personnel, and without having the positional instability of a free-standing indirect wide-angle contact lens.

In one aspect, a disclosed method for performing ophthalmic surgery includes positioning a first optical axis of a surgical microscope along a second optical axis of an eye of a patient. The method may include fitting a contact lens mounting speculum to the patient. In the method, the contact lens mounting speculum may keep eyelids of the patient open. The method may include viewing an interior portion of the eye using a contact lens in contact with the eye. In the method, the contact lens may be mechanically coupled to the contact lens mounting speculum.

In any of the disclosed embodiments of the method, the contact lens may be mechanically coupled to the contact lens mounting speculum to prevent tilting of the contact lens away from the first optical axis.

In any of the disclosed embodiments of the method, the contact lens may be mechanically coupled to the contact lens mounting speculum to enable movement of the contact lens with respect to the surgical microscope in a direction corresponding to the first optical axis.

In any of the disclosed embodiments of the method, the contact lens may be mechanically coupled to the contact lens mounting speculum to enable movement of the contact lens with respect to the surgical microscope in a direction perpendicular to the first optical axis.

In any of the disclosed embodiments of the method, fitting the contact lens mounting speculum to the patient may further include adjusting a temple mounting pad to fit the patient. In the method, the temple mounting pad may be coupled to a main body of the contact lens mounting speculum with a spherical joint.

In any of the disclosed embodiments, the method may include installing the contact lens to a mounting ring included with the contact lens mounting speculum. In any of the disclosed embodiments of the method, the contact lens mounting speculum may include wire specula. In any of the disclosed embodiments of the method, the contact lens may be an indirect contact lens.

In another aspect, a contact lens mounting speculum, includes a main body, two speculum blades extending from the main body for retracting eyelids of a patient, a temple support pad coupled to the main body, and a mounting ring coupled to the main body to position a contact lens for viewing an eye of a patient during ophthalmic surgery using a surgical microscope. IN the contact lens mounting speculum, the mounting ring may translate with respect to the main body in a first direction parallel to an optical axis of the surgical microscope.

In any of the disclosed embodiments, the contact lens mounting speculum may include a first spherical joint between the main body and the temple support pad. In any of the disclosed embodiments, the contact lens mounting speculum may include an articulated linkage, coupled to the mounting ring, for reducing friction when the mounting ring translates in the first direction.

In any of the disclosed embodiments, the contact lens mounting speculum may include a second rotation joint coupled to the articulated linkage at an opposing end from the mounting ring, an extension arm coupled to the second rotation joint, and a first rotation joint coupled to the extension arm opposite the second rotation joint. In the contact lens mounting speculum, the first rotation joint and the second rotation joint may be parallel to the first direction. In the contact lens mounting speculum, the first rotation joint and the second rotation joint may enable the mounting ring to translate in a second direction perpendicular to the first direction.

In any of the disclosed embodiments, the contact lens mounting speculum may include a second spherical joint coupled to the first rotation joint between the first rotation joint and the main body. In the contact lens mounting speculum, at least one of the first spherical joint and the second spherical joint may be compressed with a force sufficient to maintain a fixed position.

In any of the disclosed embodiments of the contact lens mounting speculum, the specula may include wire specula. In any of the disclosed embodiments of the contact lens mounting speculum, the mounting ring may include a threaded adapter to receive the contact lens. In any of the disclosed embodiments of the contact lens mounting speculum, the contact lens may be an indirect contact lens.

BRIEF DESCRIPTION OF THE DRAWINGS

For a more complete understanding of the present invention and its features and advantages, reference is now made to the following description, taken in conjunction with the accompanying drawings, in which.

DESCRIPTION OF PARTICULAR EMBODIMENT(S)

Figure 1:
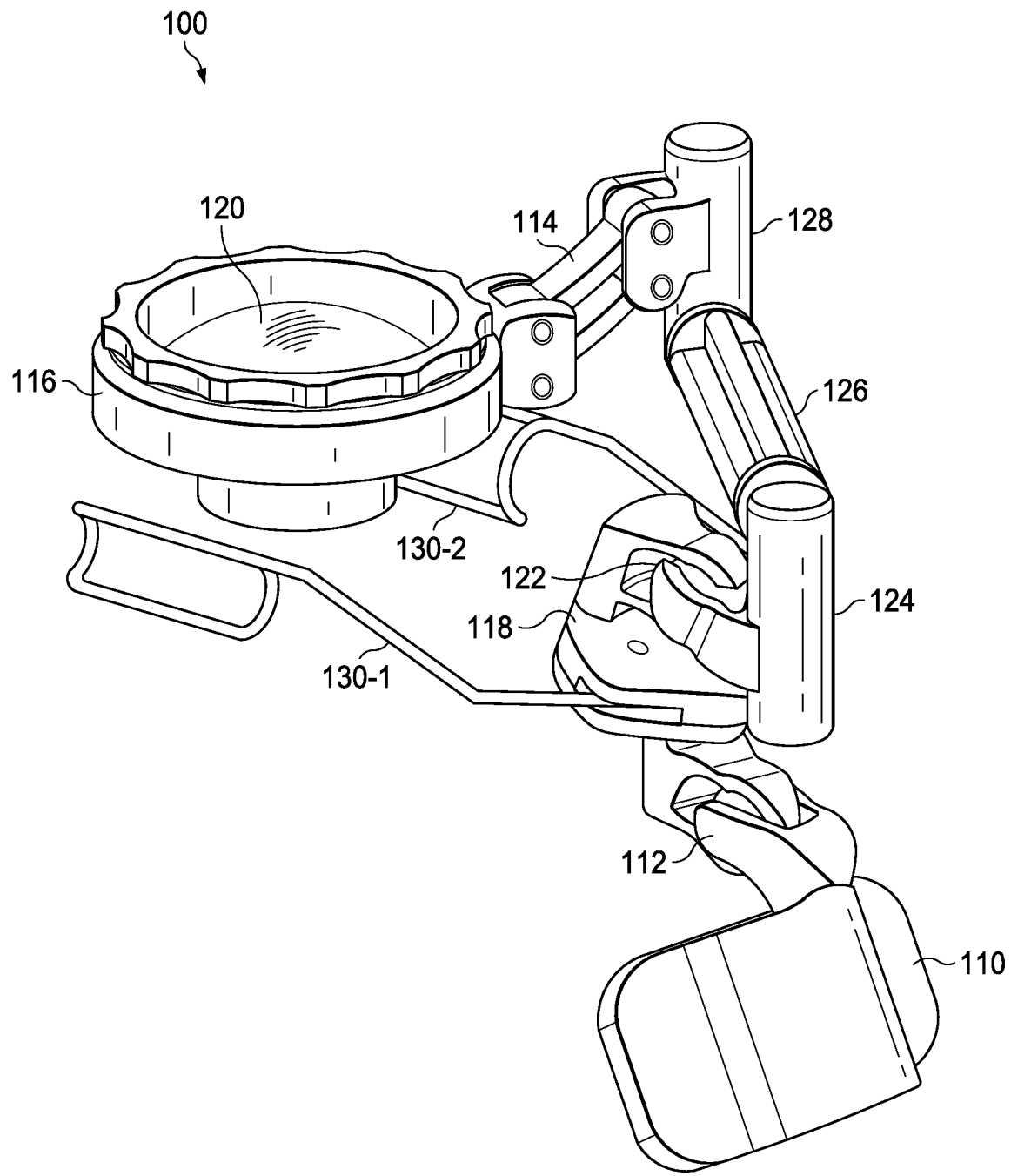
FIG. 1 is a perspective view of selected elements of an embodiment of a contact lens mounting speculum.

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

As noted above, free-standing indirect contact lenses, though they provide a much greater field of view of the fundus than other types of ophthalmic surgical lenses, are not frequently used by surgeons during vitreoretinal surgery. Because indirect contact lenses are top heavy in construction, such lenses may exhibit positional instability when resting on the cornea of a patient during surgery. Indirect contact lenses may easily lose angular and positional orientation after initial placement on the eye, resulting in repeated or continuous manual effort for repositioning during surgery. Furthermore, the instability of a typical indirect contact lens may be unpredictable during surgery, which is also undesirable.

The present disclosure relates to a contact lens mounting speculum for mechanically supporting a contact lens during ophthalmic surgery. The contact lens may be a direct contact lens or an indirect contact lens. The contact lens mounting speculum disclosed herein forces the contact lens to remain upright, and hence remain aligned with the surgeon's view through an optical axis of the surgical microscope into the eye of the patient during surgery. The contact lens mounting speculum disclosed herein may further enable the contact lens to move without substantial mechanical resistance in the horizontal and vertical directions (within certain limits) to conform to the position of the eye during surgery. In this manner, the contact lens mounting speculum disclosed herein may preserve alignment to the microscope axis for viewing through the contact lens, while retaining a certain amount of flexibility in translational movement, such as from small movements of the patient during surgery. Accordingly, the contact lens mounting speculum disclosed herein may enable the ophthalmic surgeon to enjoy the wide angle viewing capabilities afforded by indirect contact lenses, without the positional instability problems of a free-standing indirect contact lens without mechanical support, such as using additional skilled surgical personnel, and without implementing extraneous operations during surgery, such as rotating the eye or indenting the sclera to view desired portions of the fundus.

As will be described in further detail, the contact lens mounting speculum disclosed herein allows a surgeon to intraoperatively view the ocular fundus and periphery through a contact lens without assistance, by providing an adaptive articulating lens mount system that supports the contact lens and passively accommodates horizontal movement to maintain lens contact and orthogonality despite ocular rotation or movement. The adjustable and adaptive contact lens mounting speculum disclosed herein may be comprised of two spherical friction joints, two cylindrical free-rotating parallel joints, and an articulated linkage with substantially parallel members on cylindrical free-rotating parallel joints at each end. The contact lens mounting speculum described below may provide in-situ fit adjustment in a single step by the surgeon to accommodate different patient characteristics, lens heights, speculum blade types and other mounting variations. The contact lens mounting speculum described below may also provide frictionless, tilt-free passive lateral movement intra-surgically, to maintain contact of the contact lens to the patient eye as the eye is moved and rotated by the surgeon. Additionally, the contact lens mounting speculum described below is compact to preserve surgical access and can be used with the left or right eye. The contact lens mounting speculum described below may receive various commercially available surgical contact lenses (including direct and indirect contact lenses), wire speculum blades, adjustable speculum blades, or other mounting adapters, and may be relatively inexpensive to manufacture as a surgical consumable.

Figure 2:
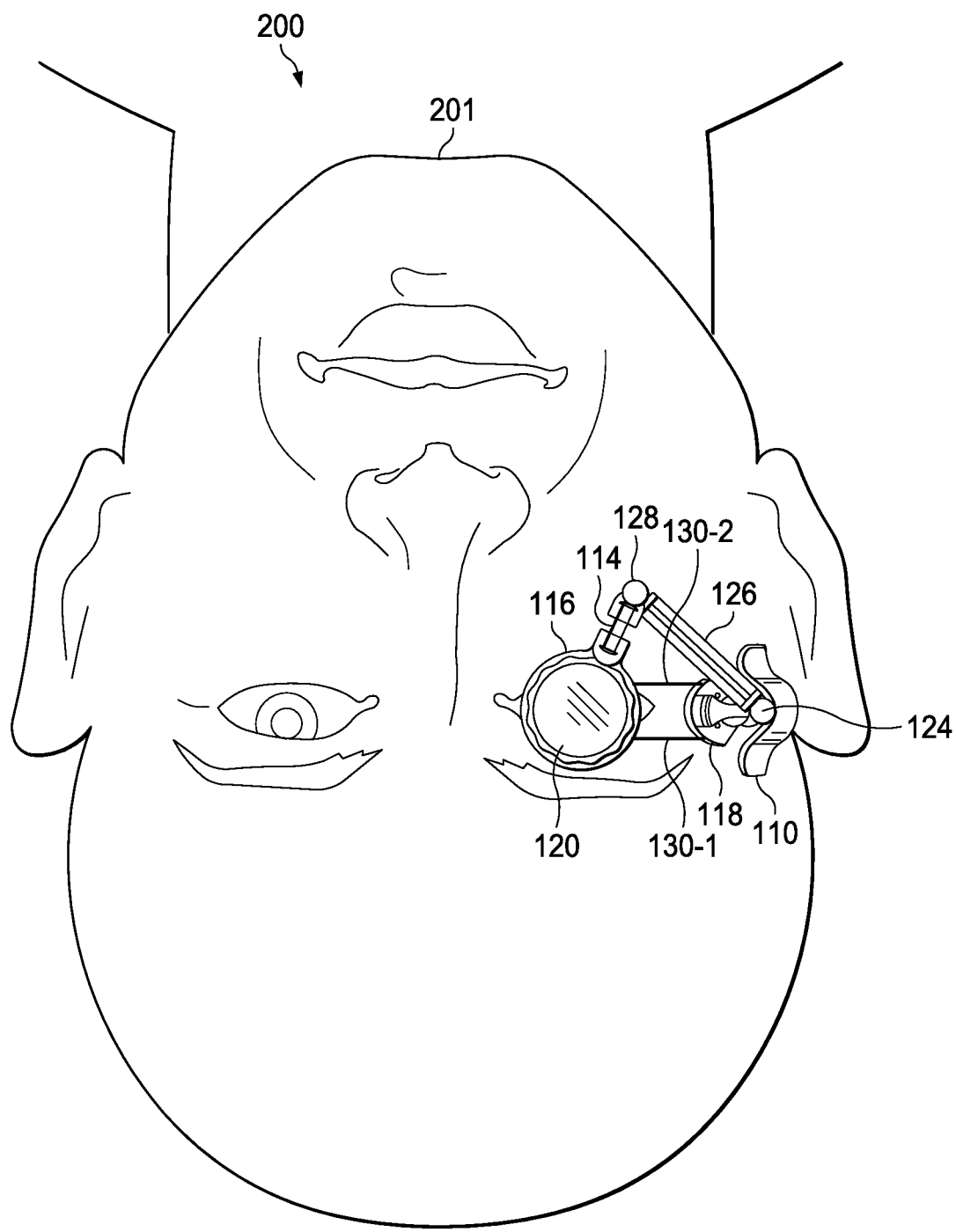
FIG. 2 is a top view of selected elements of an embodiment of a contact lens mounting speculum fitted to a patient.

Referring now to the drawings, FIGS. 1 and 2 illustrate different views of selected elements of an embodiment of a contact lens mounting speculum 100 for supporting a contact lens 120. The drawings illustrate an embodiment of contact lens mounting speculum 100 that may not be drawn to a given scale, such that particular elements included with contact lens mounting speculum 100 may be sized differently in some embodiments. Although the patient is omitted for clarity in FIG. 1, contact lens mounting speculum 100 enables a contact lens 120 to rest on an eye of a patient (see also FIGS. 2 and 3).

As will be described in further detail, FIG. 1 shows a perspective view of contact lens mounting speculum 100 with a contact lens 120 mounted thereto. It is noted that in other embodiments, different types of contact lenses, such as direct contact lenses, may be used with contact lens mounting speculum 100. Contact lens mounting speculum 100 may be made using any of a variety of materials, including metals, ceramics, and polymers. Contact lens mounting speculum 100, as shown, is comprised of a temple support pad 110, a first spherical joint 112, a main body 118, a pair of wire speculum blades 130, a second spherical joint 122, a first rotation joint 124, an extension arm 126, a second rotation joint 128, an articulated linkage 114, and a mounting ring 116 for retaining contact lens 120. In various embodiments, contact lens mounting speculum 100 may be implemented with fewer or more components than illustrated in the exemplary embodiment of FIG. 1, which is shown for descriptive purposes.

In FIG. 1, contact lens mounting speculum 100 includes temple support pad 110 coupled to main body 118 via first spherical joint 112. Temple support pad 110 may aid in supporting contact lens mounting speculum 100 to remain upright and in position. In particular, temple support pad 110 may stabilize contact lens mounting speculum 100 by counterbracing the weight of contact lens 120 while in contact with the patient's eye. Because temple support pad 110 is adjustable using first spherical joint 112, temple support pad 110 may prevent various undesired motion of contact lens mounting speculum 100, as a third supporting base point, in addition to each of wire speculum blades 130. In this manner, temple support pad 110 may provide stability and may enable contact lens mounting speculum 100 to be used with various different implementations of contact lens 120, as well as other types of contact lenses. First spherical joint 112 may act as a universal joint to enable flexible positioning of temple support pad 110 with respect to the patient. It is noted that an amount of compressive force applied to generate friction in first spherical joint 112 may be designed for a particular stabilization force that temple support pad 110 provides. In other words, first spherical joint 112 may be compressed with a force sufficient to maintain a fixed position. In some embodiments, the compressive force at first spherical joint 112 is mechanically adjustable, such as with a threaded compressive element (not shown). In some embodiments, the compressive supporting force at first spherical joint 112 is augmented by a preload force, such as may be provided by a spring or other flexible biasing element (not shown).

Also in FIG. 1 coupled to main body 118 are wire speculum blades 130, shown comprising first wire speculum blade 130-1 and second wire speculum blade 130-2. Wire speculum blades 130 are used to hold open the eyelids of the patient during vitreoretinal surgery. Wire speculum blades 130 may also provide mechanical support and stability to contact lens mounting speculum 100 by contributing to the stabilization of main body 118, particularly when applied to the eyelids of the patient. As a result, contact lens mounting speculum 100 provides both functionality to hold the eyelids of the patient open during surgery, as well as functionality to support different types of interchangeable lenses, including a flat/plano lens used for macular surgery and a wide angle lens for peripheral retinal viewing that includes multiple lenses. Such lenses are represented by a contact lens 120 in FIG. 1, which may represent a direct contact lens or an indirect contact lens. Although contact lens mounting speculum 100 is shown with wire speculum blades 130, different kinds of speculum blades may be fitted to contact lens mounting speculum 100 in place of, or in addition to wire speculum blades 130. It is noted that main body 118 may rest on the patient when contact lens mounting speculum 100 is used during vitreoretinal surgery.

Additionally attached to main body 118 is second spherical joint 122, which may be similar to first spherical joint 112 described above. Second spherical joint 122 may provide a means to orient the axes of movement of contact lens 120 by virtue of attachment via extension arm 126 and articulated linkage 114. It is noted that an amount of compressive force applied to generate friction in second spherical joint 122 may be designed for a particular stabilization force or degree of stabilization of contact lens 120. In other words, second spherical joint 120 may be compressed with a force sufficient to maintain a fixed position. In some embodiments, the compressive force at second spherical joint 122 is mechanically adjustable, such as with a threaded compressive element (not shown). In some embodiments, the compressive supporting force at second spherical joint 122 is augmented by a preload force, such as may be provided by a spring or other flexible biasing element (not shown).

Also in FIG. 1, first rotation joint 124 is situated between second spherical joint 122 and extension arm 126 to enable extension arm 126 to rotate laterally about first rotation joint 124. At an opposing end of extension arm 126, second rotation joint 128 enables articulated linkage 114 to rotate laterally about extension arm 126. First rotation joint 124 and second rotation joint 128 may be cylindrical free-rotating parallel joints. In this manner, first rotation joint 124 and second rotation joint 128 may enable lateral positioning of contact lens 120, as desired. In some embodiments, at least one of first rotation joint 124 and second rotation joint 128 may be detained, or restricted, to a certain degree of rotation, such as to a limited angular range. It is noted that an amount of friction in first rotation joint 124 and second rotation joint 128 may be selected as desired. In some embodiments, first rotation joint 124 and second rotation joint 128 may be substantially frictionless. As shown, articulated linkage 114 may be a 4-bar linkage that allows contact lens 120 to frictionlessly, or substantially frictionlessly, adapt within a range of vertical distances of the patient's eye relative to speculum blades 130, to accommodate the patient's anatomical characteristics, different lens mounting heights, and various shapes and mounting positions. Other types of linkages may be used for articulated linkage 114 in other embodiments. The contact between contact lens 120 and the patient's the eye may be provided by the weight of contact lens 120 and mounting ring 116, which rest on the eye, while a negligible amount of downward force on the eye may result from other elements of contact lens mounting speculum 100.

As shown in FIG. 1, mounting ring 116 may be fixed to an opposing end of articulated linkage 114 from second rotation joint 128. Mounting ring 116 may be enabled to receive a particular model of contact lens 120, such as by using a compliant snap-fit or using internal threads that mate with corresponding threads of contact lens 120. In some embodiments, mounting ring 116 may be replaceable for different types of contact lens 120. In particular embodiments, mounting ring 116 may receive more than one type of contact lens 120. In other embodiments, mounting ring 116 may be a different type of mechanical coupling mechanism, such as a threaded rod or hole, a clip, an insert, etc., for coupling contact lens 120 in a fixed manner to articulated linkage 114.

Accordingly, when attached to a patient, contact lens mounting speculum 100 may enable an objective of a surgical microscope to view an indirect image generated by contact lens 120, and to focus on a focal plane where the indirect image is generated. Thus, contact lens 120 is mechanically coupled to the patient using contact lens mounting speculum 100 but is still afforded a certain degree of horizontal and vertical motion with very low friction, and may accommodate different patient characteristics, different speculum blades, different lens characteristics, and different mounting positions. Contact lens mounting speculum 100 may be used to safely place contact lens 120 on the eye during vitreoretinal surgery and to hold contact lens 120 in alignment with an optical axis of the surgical microscope (see also FIG. 3), which may be aligned with an optical axis of the eye.

Although obscured from view in FIG. 1, contact lens 120 may include a concave portion that mates with the convex shape of the cornea, where an optical coupling agent may be used. The optical coupling agent may be applied as a film interfacial layer to prevent unwanted reflections and to enable viewing into the eye along its optical axis irrespective of a tilt angle of the eye axis relative to an optical axis of the surgical microscope (see also FIG. 3). The film interfacial layer created by the optical coupling agent may eliminate air bubbles at the lens-cornea interface and prevent the cornea from losing moisture. The film interfacial layer may thus function as an optical base out prism to promote enhanced viewing of peripheral regions of the fundus.

The indirect image generated by contact lens 120 at the focal plane may correspond to a field of view that is relatively wide and may extend out beyond the eye equator to the ora serrata where the retina ends. Thus, the field of view afforded by contact lens mounting speculum 100 may include a large portion of the fundus that is filled with vitreous humor, including all or most of the retina. In this manner, the surgeon is afforded a safe and stable view to perform any of a variety of surgical techniques on the eye. Furthermore, contact lens mounting speculum 100 may enable relatively quick removal and replacement of contact lens 120 on the eye, even during surgery, as desired.

Modifications, additions, or omissions may be made to surgical microscope attachment 100 without departing from the scope of the disclosure. The components and elements of contact lens mounting speculum 100, as described herein, may be integrated or separated according to particular applications. Contact lens mounting speculum 100 may be implemented using more, fewer, or different components in some embodiments.

FIG. 2 shows a top view 200 of contact lens mounting speculum 100 when resting on an eye of a patient 201. Top view 200 corresponds to a perspective of a surgeon performing vitreoretinal surgery looking down into the eye through contact lens 120 secured by contact lens mounting speculum 100, as described above. Visible in top view 200 are contact lens 120, mounting ring 116, articulated linkage 114, second rotation joint 128, extension arm 126, first rotation joint 124, wire speculum blades 130, and temple support pad 110.

Figure 3:
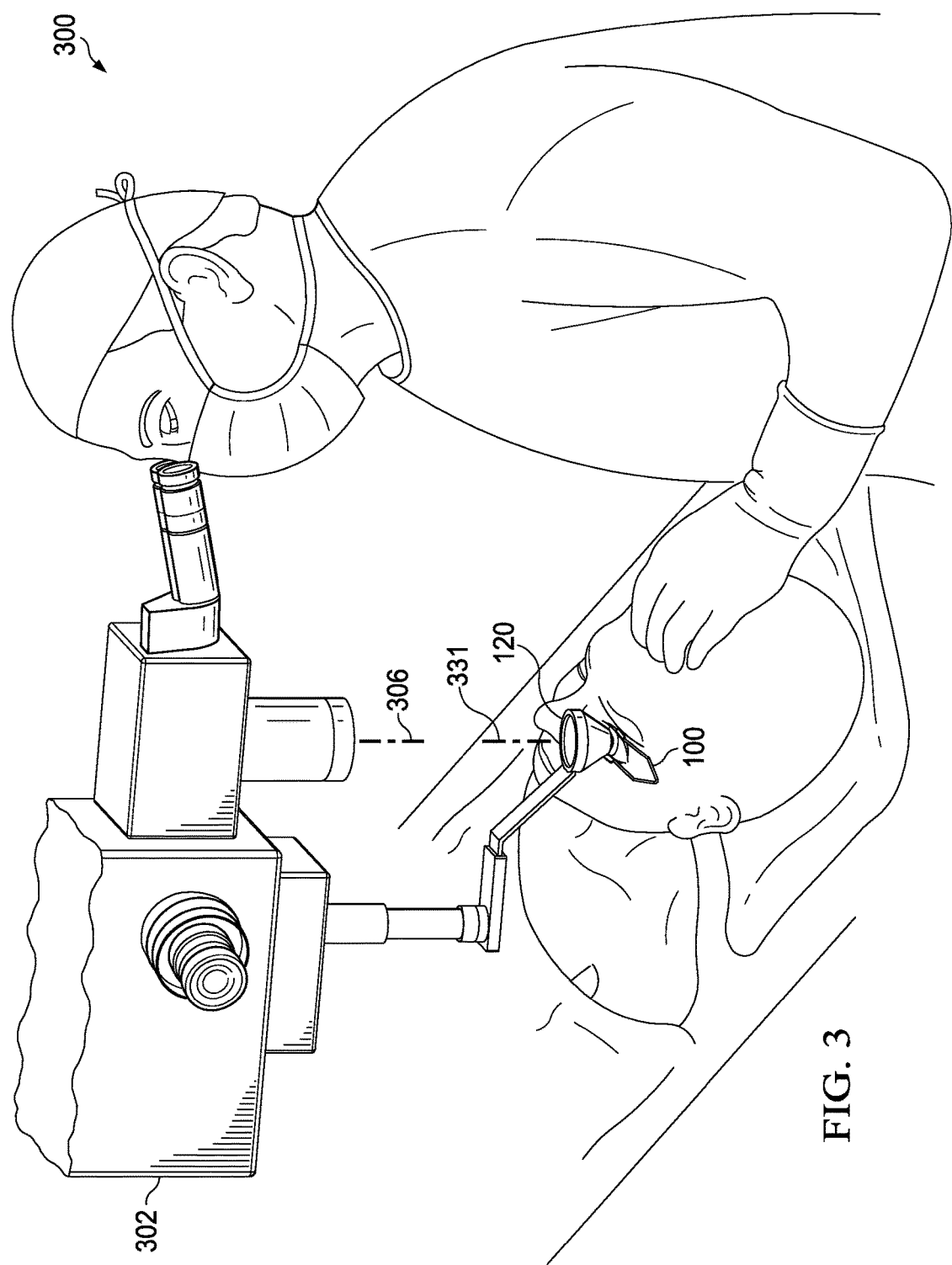
FIG. 3 is a depiction of an embodiment of a vitreoretinal surgery using a surgical microscope and a contact lens mounting speculum.

Referring now to FIG. 3, a depiction of an embodiment of a vitreoretinal surgery 300 using a surgical microscope 302 and contact lens mounting speculum 100 for supporting contact lens 120 is shown. In FIG. 3, the use of contact lens mounting speculum 100 as shown in FIG. 2 with a patent and a surgeon is depicted. Although FIG. 3 is shown with surgical microscope 302 above the patient, it is noted that different orientations of the patient with respect to surgical microscope 302 may be practiced in different embodiments.

The patient has an eye exposed using contact lens mounting speculum 100 that is in contact with contact lens 120, while the surgeon is viewing the fundus of the patient's eye using surgical microscope 102. As a result of articulated linkage 114, explained above with respect of FIG. 1, which provides low friction movement, very little vertical or horizontal pressure is extorted on the eye of the patient in vitreoretinal surgery 300. Because contact lens 120 still rests freely on the cornea, contact lens 120 may be self-retaining due to the weight of contact lens 120 transmitted to the convex portion of the cornea, which resists lateral sliding of contact lens 120 relative to the cornea. Contact lens mounting speculum 100 may ensure that contact lens 120 remains parallel to the patient's frontal plane even when the eye is rotated, by allowing for translation and height adjustment. Because the cornea and contact lens 120 mate as a ball and socket joint, contact lens 120 does not rotate with the eye, while being adjustable to different lateral positions using the articulated mechanism described herein. Therefore, when the patient's eye moves slightly relative to surgical microscope 302, contact lens 120 stays with the patient's eye and may move relative to surgical microscope 202. However, as explained previously, contact lens mounting speculum 100 may keep contact lens 120 upright and aids in maintaining alignment of optical axis 331 of contact lens 120 with an optical axis 306 of surgical microscope 302, thereby enabling useful imaging for the surgeon to be maintained during surgery without external intervention, such as by a skilled surgical technician.

Even when the optical axis 131 deviates slightly from the optical axis of the surgical microscope during vitreoretinal surgery, contact lens mounting speculum 100 may still enable useful imaging of the fundus by keeping optical axis 331 aligned with optical axis 306 of surgical microscope 302. In other words, even when optical axis 331 of the eye tilts away from optical axis 306 during vitreoretinal surgery, for example due to eye movement by the patient, contact lens mounting speculum 100 may enable the surgeon to continue viewing the fundus using contact lens 120. Furthermore, contact lens mounting speculum 100 may enable the surgeon to continue viewing the fundus without significant risk of injury to the patient that might otherwise result from an optical arrangement that is fixed and does not afford any motion of an ocular lens.

When contact lens 120 is initially placed on the eye, optical axis 331 of the eye will generally be aligned with optical axis 306 of surgical microscope 202. However, when the patient's eye makes a small movement during surgery, optical axis 331 may become slightly non-aligned with optical axis 306. Even when optical axis 306 is no longer perfectly aligned with optical axis 331, contact lens mounting speculum 100 may keep contact lens 120 upright and viewable via optical axis 306 to enable useful viewing of the fundus during surgery without interruption. In this manner using contact lens mounting speculum 100, as disclosed herein, extraneous operations to view peripheral regions of the fundus may be avoided, and additional personnel or manual actions to maintain the positional stability of contact lens 120 may be eliminated.

The objective used with surgical microscope 302 may have a focal length of about 175 mm to 225 mm that focuses on the focal plane of contact lens 120. It is noted that surgical microscope 302 may provide illumination for the fundus that is projected through contact lens 120. Thus the surgeon may be provided with a sufficient field of view via surgical microscope 202 and may safely proceed with any of a variety of vitreoretinal surgical procedures (not shown).

Figure 4:
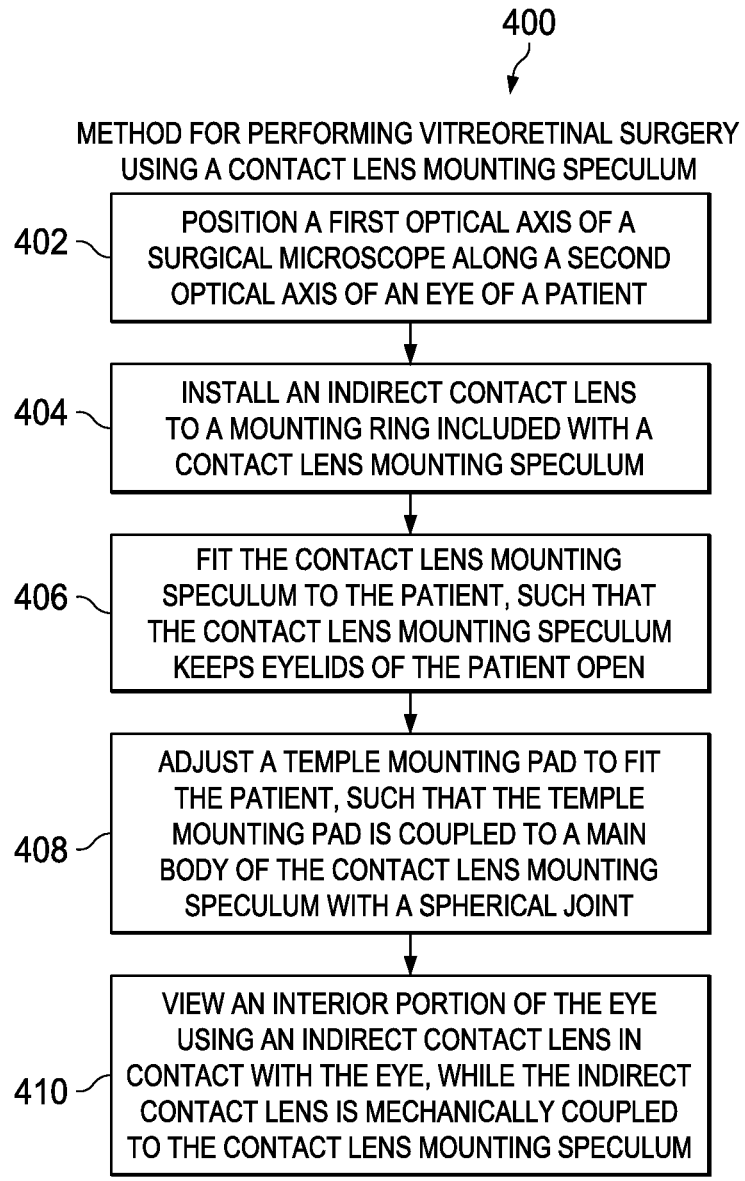
FIG. 4 is a flow chart of selected elements of a method for performing vitreoretinal surgery.

Referring now to FIG. 4, a flow chart of selected elements of an embodiment of a method 400 for performing vitreoretinal surgery, as described herein, is depicted in flowchart form. Method 400 describes steps and procedures for using contact lens mounting speculum 100 with contact lens 120 (see FIGS. 1 and 2) to view the fundus of an eye and to enable further surgical procedures based on the view of the fundus. It is noted that certain operations described in method 400 may be optional or may be rearranged in different embodiments. Method 400 may be performed by a surgeon or by other medical personnel. In some embodiments, at least certain portions of method 400 may be automated, for example using servo-mechanical control associated with certain aspects of the surgical microscope, such as raising or lowering the surgical microscope.

Method 400 may begin, at step 402, by positioning a first optical axis of a surgical microscope along a second optical axis of an eye of a patient. At step 404, the contact lens may be installed to a mounting ring included with a contact lens mounting speculum. At step 406, the contact lens mounting speculum may be fitted to the patient, such that the contact lens mounting speculum keeps eyelids of the patient open. At step 408, a temple mounting pad may be adjusted to fit the patient, such that the temple mounting pad is coupled to a main body of the contact lens mounting speculum with a spherical joint. At step 410, an interior portion of the eye may be viewed using a contact lens in contact with the eye, while the contact lens is mechanically coupled to the contact lens mounting speculum.

As disclosed herein, a contact lens is placed on a patient's eye during ophthalmic surgery, such as vitreoretinal surgery. The contact lens rests on a cornea of an eye of a patient during the surgery and is supported by a contact lens mounting speculum having multiple degrees of freedom to accommodate small movements of the eye while enabling alignment to an optical axis of the surgical microscope. The contact lens mounting speculum may be used with different patients, speculum blades, contact lenses (direct and indirect), and lens mounting positions.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A contact lens mounting speculum comprising:
    a main body;
    two speculum blades extending from the main body for retracting eyelids of a patient;
    a temple support pad coupled to the main body; and
    a mounting ring coupled to the main body to position a contact lens for viewing an eye of a patient during ophthalmic surgery using a surgical microscope, wherein the mounting ring translates with respect to the main body in a first direction parallel to an optical axis of the surgical microscope.

2. The contact lens mounting speculum of claim 1, further comprising:

a first spherical joint between the main body and the temple support pad.

3. The contact lens mounting speculum of claim 2, wherein the first spherical joint is compressed with a force sufficient to maintain a fixed position.

4. The contact lens mounting speculum of claim 1, further comprising:
an articulated linkage, coupled to the mounting ring, for reducing friction when the mounting ring translates in the first direction.

5. The contact lens mounting speculum of claim 4, further comprising:
a second rotation joint coupled to the articulated linkage at an opposing end from the mounting ring;
an extension arm coupled to the second rotation joint; and
a first rotation joint coupled to the extension arm opposite the second rotation joint.

6. The contact lens mounting speculum of claim 5, further comprising:
a second spherical joint coupled to the first rotation joint between the first rotation joint and the main body.

7. The contact lens mounting speculum of claim 6, wherein the second spherical joint is compressed with a force sufficient to maintain a fixed position.

8. The contact lens mounting speculum of claim 5, wherein the first rotation joint and the second rotation joint are parallel to the first direction.

9. The contact lens mounting speculum of claim 8, wherein the first rotation joint and the second rotation joint enable the mounting ring to translate in a second direction perpendicular to the first direction.

10. The contact lens mounting speculum of claim 1, wherein the specula further comprise wire specula.

11. The contact lens mounting speculum of claim 1, wherein the mounting ring includes a threaded adapter to receive the contact lens.

12. The contact lens mounting speculum of claim 1, wherein the contact lens is an indirect contact lens.

* * * * *